(12) United States Patent
Constantinescu et al.

(10) Patent No.: US 10,778,246 B2
(45) Date of Patent: *Sep. 15, 2020

(54) MANAGING COMPRESSION AND STORAGE OF GENOMIC DATA

(71) Applicant: International Business Machines Corporation, Armonk, NY (US)

(72) Inventors: M Corneliu Constantinescu, San Jose, CA (US); Gero Friedrich Wolf Schmidt, Mainz (DE); Wayne A. Sawdon, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/667,758

(22) Filed: Oct. 29, 2019

(65) Prior Publication Data

US 2020/0244283 A1     Jul. 30, 2020

Related U.S. Application Data

(63) Continuation of application No. 16/262,563, filed on Jan. 30, 2019, now Pat. No. 10,554,220.

(51) Int. Cl.
*H03M 7/30* (2006.01)
*G16B 30/10* (2019.01)
*G06F 16/11* (2019.01)

(52) U.S. Cl.
CPC .............. *H03M 7/70* (2013.01); *G06F 16/116* (2019.01); *G16B 30/10* (2019.02)

(58) Field of Classification Search
CPC ............................. H03M 7/70; G06F 16/116

USPC ..................................................... 341/55–90
See application file for complete search history.

(56) References Cited

U.S. PATENT DOCUMENTS

| | | | | |
|---|---|---|---|---|
| 5,406,279 | A | * | 4/1995 | Anderson ........... H03M 7/3086 341/51 |
| 5,668,598 | A | * | 9/1997 | Linzer ...................... H04N 7/52 375/240.15 |
| 5,680,129 | A | * | 10/1997 | Weinberger .......... H04N 19/593 341/65 |
| 5,784,631 | A | * | 7/1998 | Wise ..................... G06F 9/3867 382/246 |

(Continued)

FOREIGN PATENT DOCUMENTS

| | | |
|---|---|---|
| CN | 103559020 A | 2/2014 |
| WO | 2017214765 A1 | 12/2017 |
| WO | 2018068830 A1 | 4/2018 |

OTHER PUBLICATIONS

List of IBM Patents or Patent Applications Treated As Related.
(Continued)

*Primary Examiner* — Lam T Mai
(74) *Attorney, Agent, or Firm* — Zilka-Kotab, P.C.

(57) ABSTRACT

A computer-implemented method according to one embodiment includes dividing data into a plurality of partitions, creating a plurality of groups of different data types within each of the plurality of partitions, independently compressing, within each of the plurality of partitions, each of the plurality of groups of different data types to create a plurality of independently compressed partitions, and validating each of the plurality of independently compressed partitions to create a plurality of validated independently compressed partitions.

20 Claims, 4 Drawing Sheets

(56) References Cited

U.S. PATENT DOCUMENTS

| | | | |
|---|---|---|---|
| 6,204,780 B1* | 3/2001 | Cole .................... H04N 19/61 | |
| | | | 341/50 |
| 6,529,912 B2 | 3/2003 | Satoh et al. | |
| 6,657,565 B2* | 12/2003 | Kampf ................ H03M 7/3088 | |
| | | | 341/51 |
| 6,667,698 B2* | 12/2003 | Apostolopoulos ...... H03M 7/30 | |
| | | | 341/51 |
| 6,879,266 B1* | 4/2005 | Dye ........................ G06F 12/08 | |
| | | | 341/51 |
| 7,271,747 B2* | 9/2007 | Baraniuk ............. G06K 9/0057 | |
| | | | 341/50 |
| 7,366,319 B2* | 4/2008 | Andrew ................ H04N 19/70 | |
| | | | 341/56 |
| 7,444,381 B2 | 10/2008 | Malik | |
| 7,603,094 B2* | 10/2009 | Rahman .................. H04B 1/30 | |
| | | | 455/241.1 |
| 8,934,535 B2 | 1/2015 | Fallon et al. | |
| 9,519,650 B2 | 12/2016 | Lange et al. | |
| 9,892,121 B2 | 2/2018 | Mysur et al. | |
| 10,554,220 B1 | 2/2020 | Constantinescu et al. | |
| 2003/0208554 A1* | 11/2003 | Holder ................ H04L 67/2814 | |
| | | | 709/217 |
| 2004/0006433 A1* | 1/2004 | Robson .................. G16B 30/00 | |
| | | | 702/20 |
| 2005/0267693 A1* | 12/2005 | Allard .................... G16B 50/00 | |
| | | | 702/20 |
| 2017/0177602 A1* | 6/2017 | Constantinescu ... H03M 7/3077 | |
| 2017/0177603 A1* | 6/2017 | Constantinescu ... G06F 16/1744 | |
| 2017/0344578 A1* | 11/2017 | Constantinescu ... G06F 16/1727 | |
| 2018/0060485 A1* | 3/2018 | Huang ................ G06F 21/6227 | |
| 2019/0065518 A1* | 2/2019 | Constantinescu ... G06F 16/1744 | |

OTHER PUBLICATIONS

Bonfield et al., "Compression of FASTQ and SAM Format Sequencing Data," PLOS ONE, vol. 8., No. 3, Mar. 2013, pp. 1-10.
Constantinescu et al., U.S. Appl. No. 16/262,563, filed Jan. 30, 2019.
Notice of Allowance from U.S. Appl. No. 16/262,563, dated Sep. 25, 2019.
Corrected Notice of Allowance from U.S. Appl. No. 16/262,563, dated Dec. 10, 2019.

* cited by examiner

MANAGING COMPRESSION AND STORAGE OF GENOMIC DATA

BACKGROUND

The present invention relates to data compression and storage, and more specifically, this invention relates to managing compression and storage of genomic data within a system.

Genome analysis is increasing in popularity, and genomic sequencing machines are commonly used to analyze DNA and output genomic data. For example, DNA sequencing may include determining an order of nucleotides in provided DNA, and outputting genomic data representing that order. However, current methods for storing this genomic data are manual, inefficient, and subject to data loss.

SUMMARY

A computer-implemented method according to one embodiment includes dividing data into a plurality of partitions, creating a plurality of groups of different data types within each of the plurality of partitions, independently compressing, within each of the plurality of partitions, each of the plurality of groups of different data types to create a plurality of independently compressed partitions, and validating each of the plurality of independently compressed partitions to create a plurality of validated independently compressed partitions.

According to another embodiment, a computer program product for managing compression and storage of data includes a computer readable storage medium having program instructions embodied therewith, where the computer readable storage medium is not a transitory signal per se, and where the program instructions are executable by a processor to cause the processor to perform a method including dividing, by the processor, the data into a plurality of partitions, creating, by the processor, a plurality of groups of different data types within each of the plurality of partitions, independently compressing, by the processor within each of the plurality of partitions, each of the plurality of groups of different data types to create a plurality of independently compressed partitions, and validating, by the processor, each of the plurality of independently compressed partitions to create a plurality of validated independently compressed partitions.

According to another embodiment, a system includes a processor, and logic integrated with the processor, executable by the processor, or integrated with and executable by the processor, where the logic is configured to divide data into a plurality of partitions, create a plurality of groups of different data types within each of the plurality of partitions, independently compress, within each of the plurality of partitions, each of the plurality of groups of different data types to create a plurality of independently compressed partitions, and validate each of the plurality of independently compressed partitions to create a plurality of validated independently compressed partitions.

Other aspects and embodiments of the present invention will become apparent from the following detailed description, which, when taken in conjunction with the drawings, illustrate by way of example the principles of the invention.

DETAILED DESCRIPTION

The following description discloses several preferred embodiments of systems, methods and computer program products for managing compression and storage of genomic data. Various embodiments provide a method for identifying genomic data, dividing the genomic data into partitions, and compressing, validating, and storing the partitions.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

The following description discloses several preferred embodiments of systems, methods and computer program products for managing compression and storage of genomic data.

In one general embodiment, a computer-implemented method according to one embodiment includes identifying genomic data within a system, dividing the genomic data into a plurality of partitions, creating a plurality of groups of different data types within each of the plurality of partitions, independently compressing, within each of the plurality of partitions, each of the plurality of groups of different data types to create a plurality of independently compressed partitions, validating each of the plurality of independently compressed partitions to create a plurality of validated independently compressed partitions, and saving the plurality of validated independently compressed partitions within the system.

In another general embodiment, a computer program product for managing compression and storage of genomic data includes a computer readable storage medium having program instructions embodied therewith, where the computer readable storage medium is not a transitory signal per se, and where the program instructions are executable by a processor to cause the processor to perform a method including identifying, by the processor, genomic data within a system, dividing, by the processor, the genomic data into a plurality of partitions, creating, by the processor, a plurality of groups of different data types within each of the plurality of partitions, independently compressing, by the processor within each of the plurality of partitions, each of the plurality of groups of different data types to create a plurality of independently compressed partitions, validating, by the processor, each of the plurality of independently compressed partitions to create a plurality of validated independently compressed partitions, and saving, by the processor, the plurality of validated independently compressed partitions within the system.

In another general embodiment, a system includes a processor, and logic integrated with the processor, executable by the processor, or integrated with and executable by the processor, where the logic is configured to identify genomic data within a system, divide the genomic data into a plurality of partitions, create a plurality of groups of different data types within each of the plurality of partitions, independently compress, within each of the plurality of partitions, each of the plurality of groups of different data types to create a plurality of independently compressed partitions, validate each of the plurality of independently compressed partitions to create a plurality of validated independently compressed partitions, and save the plurality of validated independently compressed partitions within the system.

Figure 1:
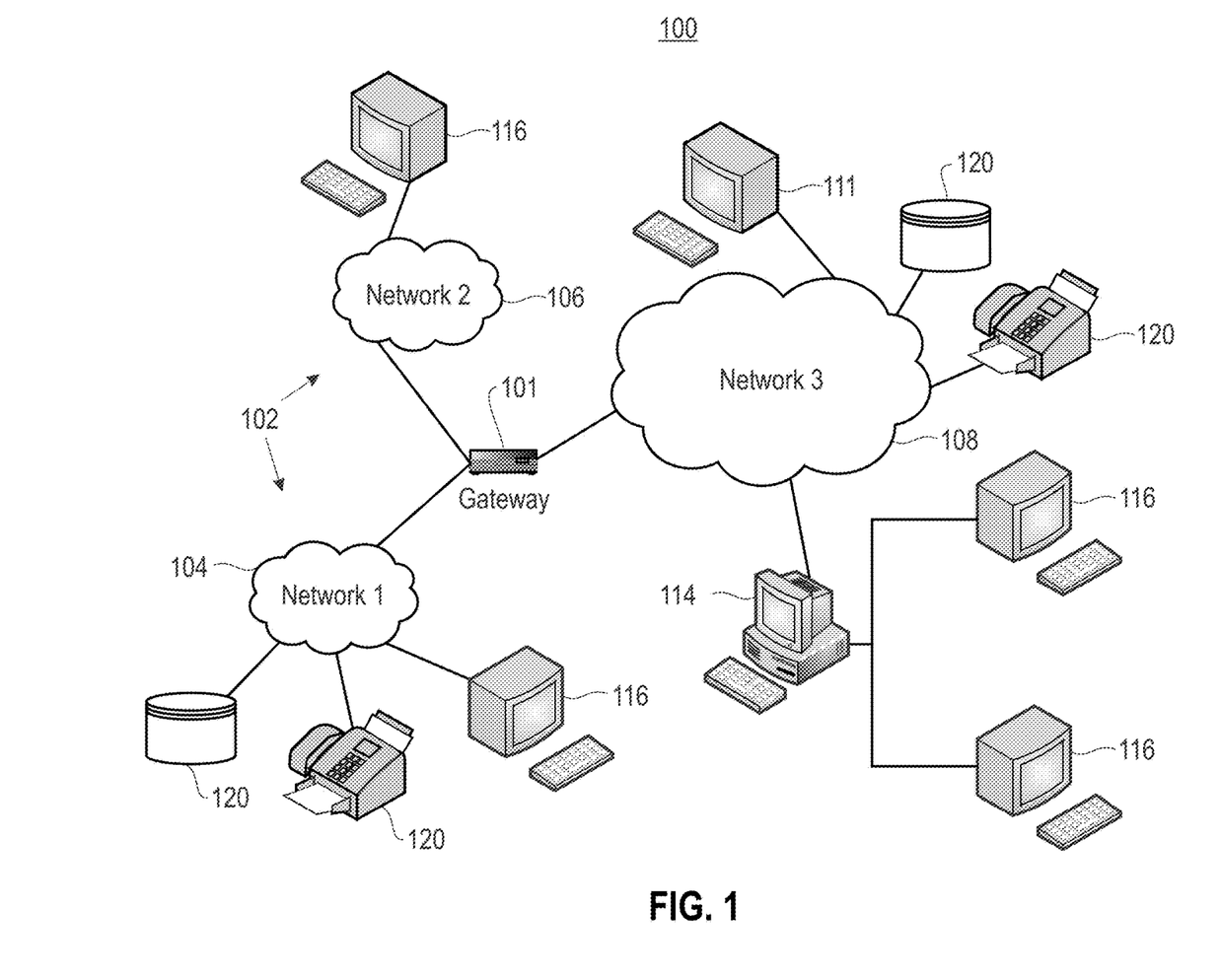
FIG. 1 illustrates a network architecture, in accordance with one embodiment.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
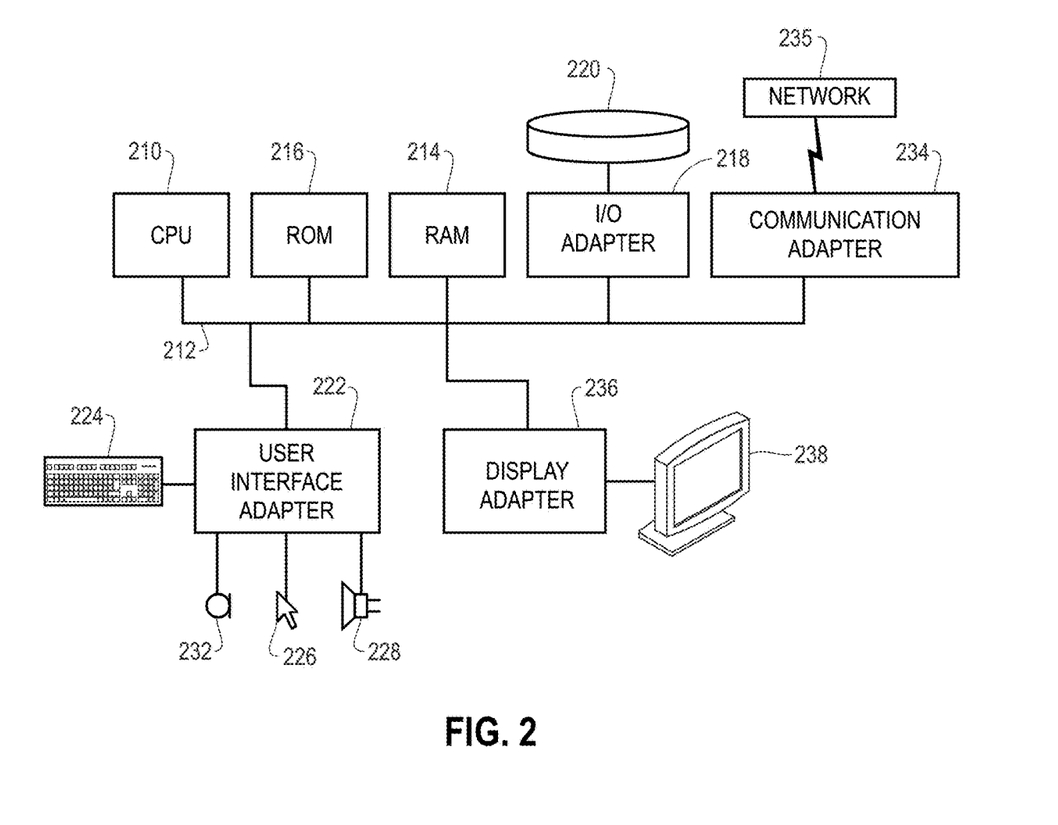
FIG. 2 shows a representative hardware environment that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

Figure 3:
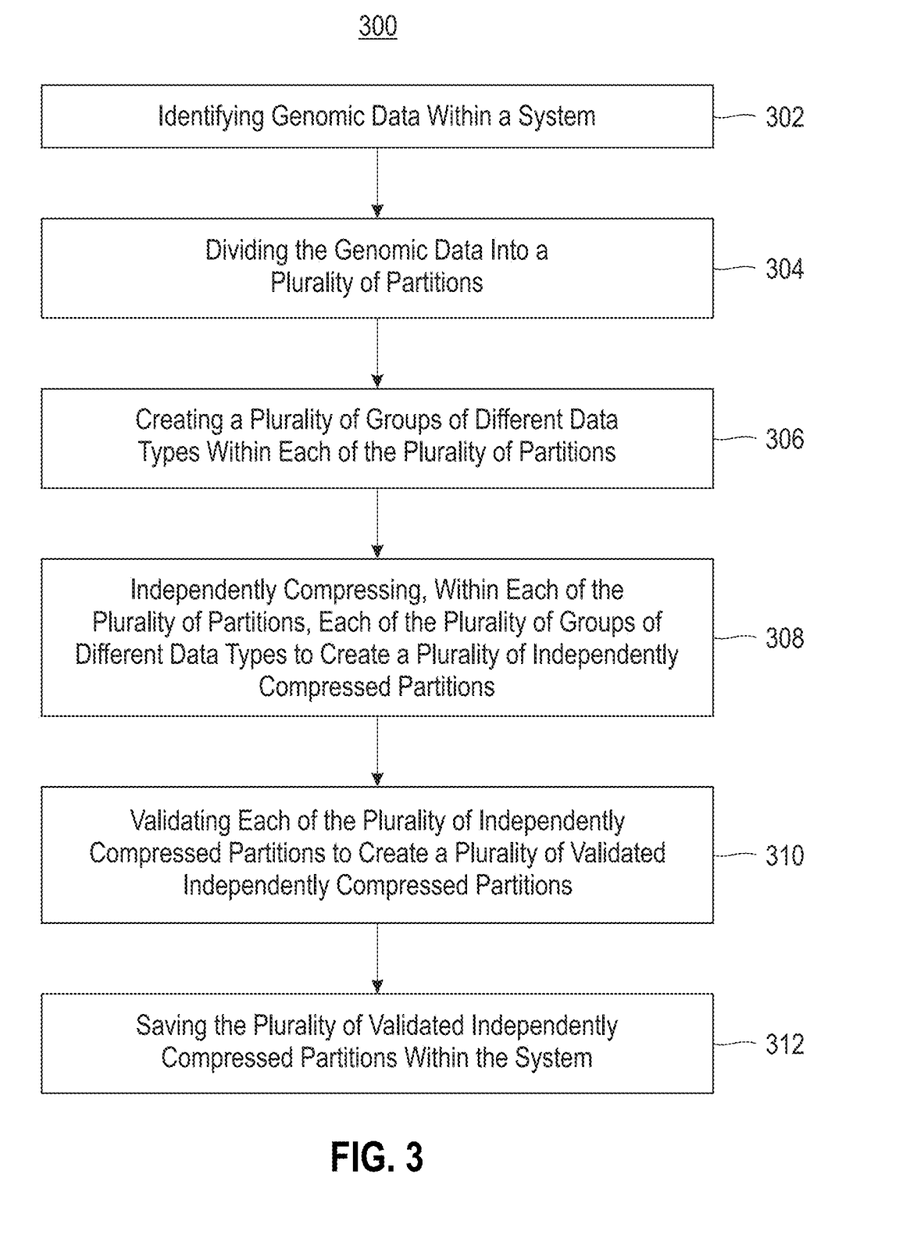
FIG. 3 illustrates a method for managing compression and storage of genomic data, in accordance with one embodiment.

Now referring to FIG. 3, a flowchart of a method 300 is shown according to one embodiment. The method 300 may be performed in accordance with the present invention in any of the environments depicted in FIGS. 1 and 2, among others, in various embodiments. Of course, more or less operations than those specifically described in FIG. 3 may be included in method 300, as would be understood by one of skill in the art upon reading the present descriptions.

Each of the steps of the method 300 may be performed by any suitable component of the operating environment. For example, in various embodiments, the method 300 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 300. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 3, method 300 may initiate with operation 302, where genomic data is identified within a system. In one embodiment, the genomic data may be identified in response to receipt of the genomic data at the system. In another embodiment, the genomic data may be identified in response to creation of the genomic data at the system. In yet another embodiment, the genomic data may be identified in response to a request to save the genomic data at the system.

Additionally, in on embodiment, the genomic data may include deoxyribonucleic acid (DNA) sequencing data. For example, the genomic data may include DNA sequencing data generated by one or more sequencing machines. In another embodiment, the system may include a distributed file system. For example, the system may allow multiple different users access to data from multiple different hosts within the system.

Further, in one embodiment, the genomic data may include a single file created as a result of one or more biological sequencing operations. In another embodiment, identifying the genomic data may include determining a file type and/or a file extension for data. For example, genomic data may include data having a FASTQ format, a FASTQ file extension (e.g., ".fq," ".fastq,"), etc. In another example, genomic data may include data having a sequence alignment map (SAM) format, a SAM file extension, etc. In yet another example, the genomic data may include a text-based format that stores a biological sequence (e.g., a nucleotide sequence, etc.) and corresponding quality scores.

Further still, in one embodiment, the genomic data may be automatically identified within the system. In another embodiment, a preliminary compression may be performed on a portion of data to verify that the data is in fact genomic data. For example, one or more partitions may be preliminarily compressed utilizing one or more special-purpose compression libraries. In another example, during the preliminary compression, the compression algorithm may analyze the data being compressed (e.g., by comparing a format of the preliminary compression to a format of compressed genomic data, etc.). In yet another example, if the data being compressed does not conform to a predetermined format (e.g., a FASTQ format, a SAM format, etc.), the data may be compressed utilizing a general-purpose compression algorithm (e.g., zstd, zlib, etc.).

Also, method 300 may proceed with operation 304, where the genomic data is divided into a plurality of partitions. In one embodiment, the genomic data may be divided into partitions, where each of the partitions has the same size as the other partitions (e.g., 32 KB, etc.). In another embodiment, the genomic data may be divided into partitions (e.g., partitions of a genomic sequence represented by the genomic data), such that each of the plurality of partitions include data having a plurality of predetermined types. For example, each predetermined type of data may be represented as a distinct line within the genomic sequence.

For example, a FASTQ file may include four lines per sequence:
Line 1 begins with a '@' character and is followed by a sequence identifier and an optional description (e.g., a FASTA title line, etc.).
Line 2 includes raw sequence letters.
Line 3 begins with a '+' character and is optionally followed by the same sequence identifier (and any description) again.
Line 4 encodes quality values for the sequence in Line 2, and contains the same number of symbols as letters in the sequence.

In one embodiment, the genomic data within each partition may include these four lines of data.

In addition, method 300 may proceed with operation 306, where a plurality of groups of different data types are created within each of the plurality of partitions. In one embodiment, the plurality of groups may be created by grouping similar types of data together within each of the plurality of partitions. In another embodiment, each of the plurality of partitions may include data of a plurality of different types. In yet another embodiment, each of the plurality of partitions may include data organized into a plurality of reads.

Furthermore, in one embodiment, each of the plurality of reads may include a plurality of lines (e.g., four different lines, where each line represents a different type of data). In another embodiment, the genomic data may be grouped such that each of the plurality of groups contains data of a single type. For example, the first group of data may include all first line data for all reads within a sequence, the second group of data may include all second line data for all reads within a sequence, the third group of data may include all third line data for all reads within a sequence, and the fourth group of data may include all fourth line data for all reads within a sequence.

Further still, method 300 may proceed with operation 308, where within each of the plurality of partitions, each of the plurality of groups of different data types are independently compressed to create a plurality of independently compressed partitions. In one embodiment, each of the plurality of groups of different data types may be compressed separately from the other groups using a compression algorithm different from the other groups, to create a plurality of compressed groups. In this way, each compressed partition may include a plurality of compressed groups.

Also, in one embodiment, the compression algorithm used to compress each of the plurality of groups may be specific to the genomic data stored within that group. For example, if data within a group includes only alphabetic characters, Huffman encoding may be used to compress the genomic data within the group. In another example, if data within a group includes only ASCII sequences, arithmetic encoding may be used to compress the genomic data within the group. In this way, improved compression may be achieved within each of the plurality of partitions.

Additionally, in one embodiment, compression may be performed within each of the plurality of partitions in parallel. In another embodiment, metadata may be added to one or more of the plurality of independently compressed partitions, where the metadata for a compressed partition describes a location of the compressed partition within a sequence of the genomic data.

Further, method 300 may proceed with operation 310, where each of the plurality of independently compressed partitions are validated to create a plurality of validated independently compressed partitions. In one embodiment, validating each of the plurality of independently compressed partitions may be performed during the compressing of each of the plurality of independently compressed partitions. In another embodiment, for each of the plurality of independently compressed partitions, validating each of the plurality of independently compressed partitions may include decompressing the compressed partition to create decompressed data, and comparing the decompressed data to the original partition before it was compressed.

Further still, in one embodiment, within each compressed partition, each of the plurality of compressed groups may be decompressed. In another embodiment, the decompressed groups may be compared to the original groups within the partition prior to compression. In yet another embodiment, if the decompressed data matches the original partition, the compressed partition is validated.

Also, in one embodiment, a validated compressed partition may also be hashed to create a hash value that is stored with the validated compressed partition (e.g., as metadata, etc.). For example, a hashing algorithm may be applied to the validated compressed partition to create the hash value. In another example, the hash value may be used to ensure data integrity when the compressed partition is later recalled and decompressed.

In this way, data integrity may be ensured during the compression and storage of each partition. In one embodiment, if the decompressed data does not match the original partition, the compressed partition is not validated, and the corresponding original partition is stored without being compressed. In this way, validating each of the plurality of independently compressed partitions may result in a plurality of validated independently compressed partitions and one or more non-validated independently compressed partitions.

In addition, method 300 may proceed with operation 312, where the plurality of validated independently compressed partitions are saved within the system. In one embodiment, each of the plurality of validated independently compressed partitions may be saved with their corresponding hash within the system. In another embodiment, any non-validated independently compressed partitions may not be saved within the system. Instead, the original partitions corresponding to the non-validated independently compressed partitions may be saved within the system.

Furthermore, in one embodiment, one or more of the above actions may be performed automatically/transparently to one or more users within the system. For example, one or more application programming interfaces (APIs) may be used as an extension of the system to automatically/transparently identify genomic data within the system, divide the genomic data into a plurality of partitions, create groups within the partitions, independently compress the groups, validate the independently compressed partitions, and save the validated independently compressed partitions.

Further still, in one embodiment, random access may be provided to one or more of the validated independently compressed partitions. For example, a request for a predetermined portion of the genomic data may be received, and a subset of the validated independently compressed partitions may be determined that contain the requested predetermined portion of the genomic data. These determined partitions may then be decompressed to obtain the predetermined portion of the genomic data, which may then be returned in response to the request.

In this way, validated independently compressed partitions of genomic data may be stored instead of one large compressed file representing all of the genomic data. This may reduce an amount of time and resources needed to access a random portion of the compressed genomic data. For example, in response to receiving a user request for a specific portion of genomic data, only a portion of a stored genomic data file (e.g., one validated compressed partition of the genomic data, etc.) may be determined to include specific requested portion of genomic data, and such portion of the stored genomic data file may be decompressed and provided to the user in response to the determination, instead of the entire genomic data file. This selective partial decompression may therefore improve a performance of the system during requested data access/decompression.

Additionally, identified genomic data may be dynamically/automatically compressed, validated, and stored as transparent file system operations, which may ensure a quality of the genomic data and reduce data errors within the system, and which may improve a performance and security of the system. Further, compression may be customized within individual groups of data within each partition, which may minimize a size of stored data, and may thereby maximize a storage utilization of the system, which may improve a performance and efficiency of the system.

Figure 4:
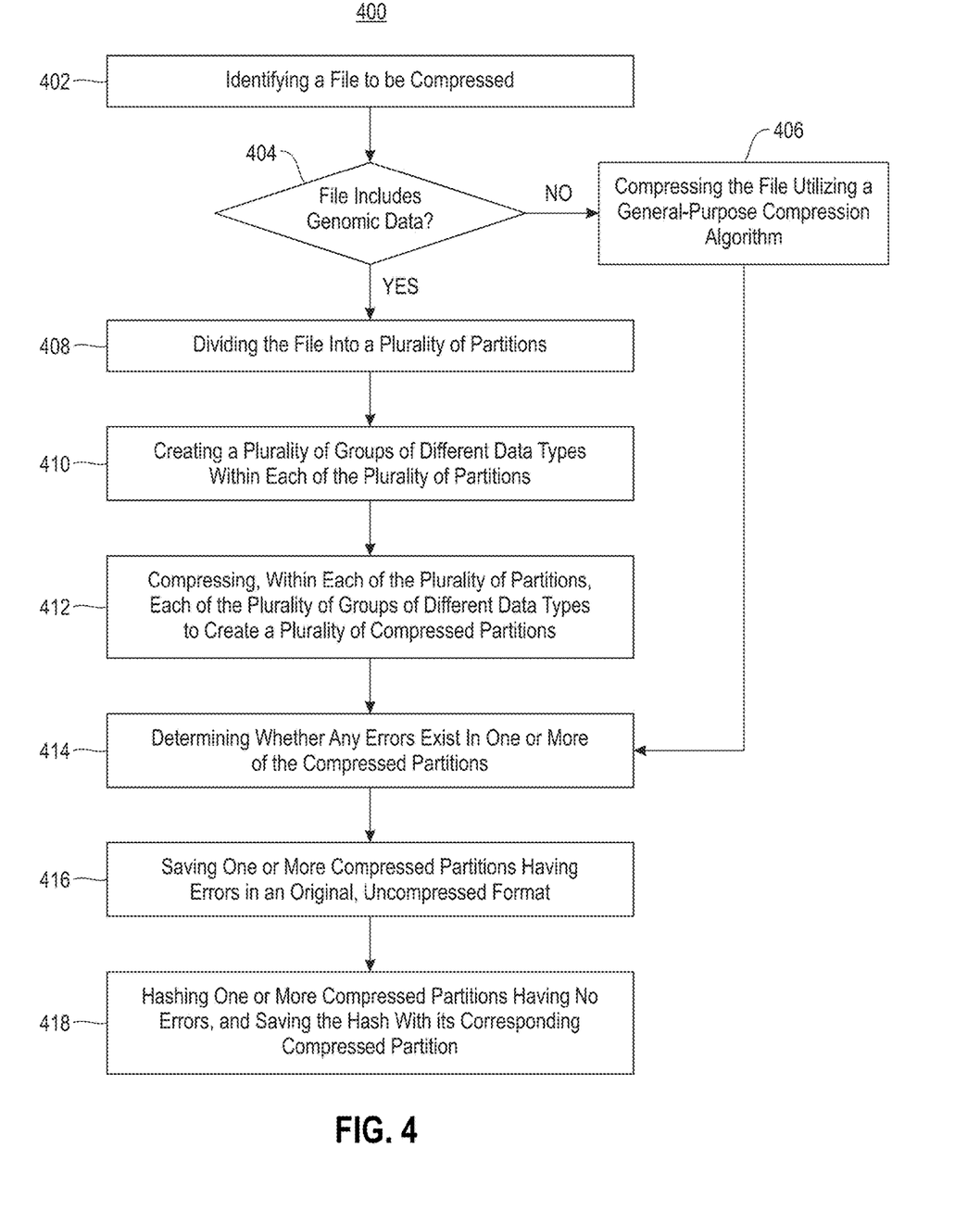
FIG. 4 illustrates a method for compression of a file including genomic data, in accordance with one embodiment.

Now referring to FIG. 4, a flowchart of a method 400 for compression of a file including genomic data is shown according to one embodiment. The method 400 may be performed in accordance with the present invention in any of the environments depicted in FIGS. 1 and 2, among others, in various embodiments. Of course, more or less operations than those specifically described in FIG. 4 may be included in method 400, as would be understood by one of skill in the art upon reading the present descriptions.

Each of the steps of the method 400 may be performed by any suitable component of the operating environment. For example, in various embodiments, the method 400 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 4, method 400 may initiate with operation 402, where a file to be compressed is identified. Additionally, method 400 may proceed with decision 404, where it is determined whether the file includes genomic data. For example, the determining may include comparing a file type and/or a file extension for the file to a list of file types and/or extensions associated with genomic data. In another example, the determining may include performing a preliminary compression on a portion of the file, and analyzing the compressed portion to determine if the compressed portion is similar to compressed genomic data.

Additionally, in response to determining in decision 404 that the file does not include genomic data, method 400 may proceed with operation 406, where the file is compressed utilizing a general-purpose compression algorithm. In response to determining in decision 404 that the file does includes genomic data, method 400 may proceed with operation 408, where the file is divided into a plurality of partitions.

Further, method 400 may proceed with operation 401, where a plurality of groups of different data types are created within each of the plurality of partitions. Further still, method 400 may proceed with operation 412, where within each of the plurality of partitions, each of the plurality of groups of different data types is compressed to create a plurality of compressed partitions.

Also, method 400 may proceed with operation 414, where it is determined whether any errors exist in one or more of the compressed partitions. The determination may include decompressing the compressed partition to create decompressed data, and comparing the decompressed data to the original partition before it was compressed to identify any errors between the data.

In addition, method 400 may proceed with operation 416, where one or more compressed partitions having errors are saved in an original, uncompressed format. Furthermore, method 400 may proceed with operation 418, where one or more compressed partitions having no errors are hashed, and the hash is saved with its corresponding compressed partition.

In this way, the file may be independently and transparently compressed in the background at any time to save storage space without interfering with a genomic pipeline.

Fast and Efficient Transparent Compression of Genomic Data in File Systems

Overview

In one embodiment, genomic DNA sequencing data generated by next generation sequencing (NGS) machines is represented in FASTQ format and usually compressed with gzip. Just an individual file is hundreds of GB in size and compression/decompression with gzip is slow. Researchers work on the files in compressed and uncompressed formats and have to manually compress/decompress them using gzip or other methods of choice that can be unreliable. The infrastructure team cannot compress and rename files independently in the background to save space without actually interfering with the user jobs.

In another embodiment, for processing this data (usually hundreds of GB in size), the files are uncompressed and fed to genomic analysis pipelines where some large intermediate files are generated (in SAM/BAM format) until smaller result files, e.g. in VCF format, are obtained. The growing storage demand of genomic data files poses a major concern and challenge to IT infrastructure teams of businesses in the genomic sequencing domain today. Efficient, transparent compression of FASTQ data at all times with no additional manual interaction is therefore desired.

Another important advantage of using transparent genomic compression is improved compressed data integrity. For example, instead of users using ad hoc genomic compression algorithms with potential flaws that might lead to data loss, the compression is transparently performed by the file system that can provide strong data integrity for compressed data. Compressed data integrity seems to be one reason biologists keep using gzip to compress genomic data.

There are some file systems that support compression (like zfs or btrfs) but they support only general-purpose compression (like zlib/gzip/lz4) that doesn't work well on genomic data.

There is therefore a need to provide fast, reliable and efficient transparent genomic data compression in file systems for businesses in the genomic sequencing or genomic analysis domains. This enables the reliable use of flexible special purpose genomic compression methods that provide better compression ratios and speeds exploiting specific data types. The integrity of compressed data and the correctness of the compression algorithm can be enforced by the file system and may not include an ad-hoc, unsupported genomic compression algorithms users may choose.

SUMMARY

In one embodiment, transparent genomic data compression/decompression methods may be provided in a file system that autonomically selects the appropriate compression method to be used based on the file type. Our special purpose genomic compression may be faster and more efficient than the general-purpose compression algorithms that may be available in other file systems and the policy engine in combination with pluggable compression libraries makes the compression autonomic and transparent. The algorithm detailed in the next section checks if the type of data in the file conforms with genomic data formats (FASTQ, SAM) and if not, it "falls back" to using a general-purpose compression algorithm (like zstd or zlib) to compress the file. The genomic compression algorithm provides fast random access to compressed data for reads and writes so the genomic data files can be processed transparently while being stored in a compressed format.

In another embodiment, for strong integrity checking, each compressed partition can optionally be decompressed and compared to the original uncompressed partition during compression to ensure data integrity. If a compressed partition should fail the data integrity check due to a flaw in the compression library chosen for a specific format, it will be stored uncompressed to avoid data loss. If the comparison passes, a hash of the raw partition (that in one embodiment can be a CRC32C) is added to the compressed partition code, and the compressed partition is stored in the compressed file. During decompression, the hash is recomputed after the partition is decompressed, and the hash is checked with the stored hash to identify any data corruption occurring during storage.

Exemplary Details

In one embodiment, a file system may enable dynamic linking of various compression libraries. For example, this flexibility can be implemented by defining a common compression API, where each compression library uses this common API for compression and decompression. Genomic data files represented in FASTQ or SAM formats (or other predetermined formats including genomic data) have a specific name extension (".fastq," ".fq," ".sam," etc,) that can be used by a policy engine to select the appropriate special purpose compression library for compressing each type of file. In absence of unique file name conventions, more sophisticated algorithms may be applied in conjunction with the policy engine to properly identify FASTQ or SAM files based on their defined structure by reading the initial blocks of a file and properly tagging them as FASTQ or SAM files.

Additionally, in one embodiment, after selecting the file to be compressed (e.g., by file name extension or content), the compression algorithm may check if the data format of the file is compliant with FASTQ (or SAM). In one embodiment, this may be performed by counting the row lengths and number of rows in a read/record action for the file. If noncompliance is determined, the genomic compression algorithm may "fall back" to using a general-purpose compression algorithm (e.g., zstd, etc.) and marks the algorithm used in compressed partition metadata.

Further, in one embodiment, the genomic compression method may provide fast random reads (e.g., during decompression) and random writes (e.g., during compression) so that the file system works transparently with compressed genomic data as if it was raw data. In one embodiment, support for random access is implemented by independently compressing/decompressing small blocks (partitions) of genomic data file (e.g., 32 KB blocks, etc.). This solution has the advantage of parallelism where partitions can be compressed and decompressed in parallel.

Further still, in one embodiment, compression of data in a partition improves when subsets of data of the same type (e.g., headers, sequences, quality values, etc.) are compressed together. For example, the "reads" in FASTQ (and records in SAM) may be composed of different types of data: headers, nucleotide sequences, quality values, position information, etc. These subsets (called rows) may be detected and concatenated together into "columns," in one embodiment creating four such columns for FASTQ and twelve for SAM.

Also, in one embodiment, a plurality of rows of similar content may be grouped and compressed together either interleaved or one after the other, and may therefore increase the amount of data that is independently compressed, as well as optimizing the amount of temporary memory used.

In addition, in one embodiment, compression of data in each column may be done using a single compression algorithm (like zlib, zstd or lz4). In another embodiment, compression of data uses a specific method for each column (e.g., zstd for first and third column and Huffman or arithmetic coding for a second and fourth column (sequences and quality values, respectively) in FASTQ. In another embodiment, the use of arithmetic coding to compress the sequences (e.g., in the second column) is based on a simple heuristic that doesn't involve any additional work. For example, if the highest frequency symbol crosses a threshold (e.g., 60%), then arithmetic coding is used, otherwise Huffman coding is used during compression.

Furthermore, in one embodiment, a Huffman coding of sequences may use an "alphabet extension" where each coded symbol is composed of more than one nucleotide. In all above compression variants, the compression of columns inside each partition may be done in parallel.

Further still, in one embodiment, given that independent compression is performed on partitions that can be at arbitrary offsets in the genomic data file, the ID of the first compressed column may be stored in metadata of the compressed partition. This minimal addition of metadata may enable FASTQ or SAM format awareness and the selection of different algorithms for different columns in the partition. Additionally, to improve robustness, the compressed size and row size of each column (e.g., in bytes) may be stored in the associated compressed partition header.

Also, in one embodiment, decompression of each column may be performed in parallel using the correct algorithm specified in partition metadata. After decompression, the columns may be re-arranged as rows to get lossless compression.

Additionally, in one embodiment, for strong integrity checking, each compressed partition may be decompressed and compared with the original uncompressed partition while being compressed to ensure data integrity. If a compressed partition should fail the data integrity check due to a flaw in the compression library chosen for a specific format, it may not be stored compressed to avoid data loss. If the comparison passes the data integrity check, then a hash of the raw partition (e.g., a CRC32C, etc.) may be added to the compressed partition code. The compressed partition may then be stored in the compressed file. At decompression, the hash may be recomputed after the partition is decompressed, and the recomputed hash may be checked with the stored hash to identify potential data corruption.

In one embodiment, a flexible common compression API may be incorporated into a file system that enables linking at run time of special purpose compression libraries (ex. for genomic data). This makes the special purpose compression autonomic and transparent.

The compression algorithms may be designed to enable random access reads and writes to compressed data in order to work transparently and fast inside the file system. One way to provide random access is to compress data in relatively small blocks/partitions. This solution also enables parallel compression of the partitions providing parallelism for larger files.

Additionally, the correctness of the compression method may be checked, as well as the integrity of compressed data. Given that the special purpose compression methods are implemented by users interested in transparently compressing a special type of data (ex. genomic), the file system may (optionally) check the correctness of the compression method by decompressing each partition (e.g., immediately after compression, etc.) and computing a hash (e.g., a CRC32C hash, etc.) on the raw and decompressed partition. If the hashes match, the compressed partition is stored together with the hash, and the integrity or the compressed stream is then checked at decompression.

In one embodiment, the appropriate special purpose genomic compression method to be used may be autonomically and transparently selected based on the file type. In another embodiment, it may be determined (in the compression algorithm), whether the data content conforms with the genomic data format (FASTQ or SAM); if the data content does not conform, a general-purpose compression algorithm such as zstd (or zlib) may be used to compress the file.

In yet another embodiment, partitions of genomic data file are independently compressed (to support random access and parallelism), and data inside partitions can be regrouped based on content (header, nucleotide sequences or quality values) and compressed with the same or different algorithms for each type of content. Metadata (e.g., compressed partition size, content group size, content group ID, etc.) may be added to the compressed partition to enable fast and robust decompression.

In one embodiment, a system and compression method may include a transparent compression in a file system, using a common API to dynamically link to a running file system with pluggable compression libraries, autonomously selecting the appropriate special purpose genomic compression method to be used based on the file type (identified by the data format within the file), enabling fast random access (read/write) to compressed data (without first decompressing the whole data), detecting if the data content does not conform to the genomic data format, and falling back on using a general purpose compression algorithm (like zstd or zlib) in response to the detecting. In another embodiment, the method may check the correctness of the compression/decompression method and the integrity of compressed data.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A computer-implemented method, comprising:
dividing data into a plurality of partitions;
creating a plurality of groups of different data types within each of the plurality of partitions;
independently compressing, within each of the plurality of partitions, each of the plurality of groups of different data types to create a plurality of independently compressed partitions; and
validating each of the plurality of independently compressed partitions to create a plurality of validated independently compressed partitions.

2. The computer-implemented method of claim 1, further comprising determining a file type for the data, a file extension for the data, or a file type and a file extension for the data.

3. The computer-implemented method of claim 1, further comprising performing a preliminary compression on a portion of the data to verify the data.

4. The computer-implemented method of claim 1, wherein the independent compressing is transparently performed within a system.

5. The computer-implemented method of claim 1, wherein the plurality of groups of different data types are created by grouping similar types of data together within each of the plurality of partitions.

6. The computer-implemented method of claim 1, wherein each of the plurality of partitions includes data of a plurality of different types.

7. The computer-implemented method of claim 1, wherein the data is grouped such that each of the plurality of groups of different data types contains data of a single type.

8. The computer-implemented method of claim 1, wherein each of the plurality of groups of different data types is compressed using a compression algorithm different from the other groups, to create a plurality of compressed groups.

9. The computer-implemented method of claim 1, wherein each compressed partition includes a plurality of compressed groups.

10. The computer-implemented method of claim 1, wherein a compression algorithm used to compress each of the plurality of groups of different data types is specific to the data stored within that group.

11. The computer-implemented method of claim 1, wherein compression is performed within each of the plurality of partitions in parallel.

12. The computer-implemented method of claim 1, wherein metadata is added to one or more of the plurality of independently compressed partitions, where the metadata for a compressed partition describes a location of the compressed partition within a sequence of the data.

13. The computer-implemented method of claim 1, wherein validating each of the plurality of independently compressed partitions is performed during the compressing of each of the plurality of independently compressed partitions.

14. The computer-implemented method of claim 1, further comprising providing random access to one or more of the validated independently compressed partitions.

15. The computer-implemented method of claim 1, wherein for each of the plurality of independently compressed partitions, validating each of the plurality of independently compressed partitions includes decompressing the independently compressed partition to create decompressed data, and comparing the decompressed data to an original partition before it was compressed.

16. The computer-implemented method of claim 15, wherein the independently compressed partition is validated in response to determining that the decompressed data matches the original partition.

17. The computer-implemented method of claim 16, further comprising hashing a validated compressed partition to create a hash value that is stored with the validated compressed partition.

18. The computer-implemented method of claim 15, further comprising storing a corresponding original partition without being compressed in response to determining that the decompressed data does not match the original partition.

19. A computer program product for managing compression and storage of data, the computer program product comprising a computer readable storage medium having program instructions embodied therewith, wherein the computer readable storage medium is not a transitory signal per se, the program instructions executable by a processor to cause the processor to perform a method comprising:
dividing, by the processor, the data into a plurality of partitions;
creating, by the processor, a plurality of groups of different data types within each of the plurality of partitions;
independently compressing, by the processor within each of the plurality of partitions, each of the plurality of groups of different data types to create a plurality of independently compressed partitions; and
validating, by the processor, each of the plurality of independently compressed partitions to create a plurality of validated independently compressed partitions.

20. A system, comprising:
a processor; and
logic integrated with the processor, executable by the processor, or integrated with and executable by the processor, the logic being configured to:
divide data into a plurality of partitions;
create a plurality of groups of different data types within each of the plurality of partitions;
independently compress, within each of the plurality of partitions, each of the plurality of groups of different data types to create a plurality of independently compressed partitions; and
validate each of the plurality of independently compressed partitions to create a plurality of validated independently compressed partitions.

* * * * *